United States Patent [19]

Herr et al.

[11] Patent Number: 5,047,508
[45] Date of Patent: Sep. 10, 1991

[54] MONOCLONAL ANTIBODY TO MHS-5; A NEW PROBE FOR SEXUAL ASSAULT ANALYSIS

[75] Inventors: John C. Herr; Mark Sigman; William M. Sutherland, all of Charlottesville, Va.

[73] Assignee: The University of Virginia Alumni Patents Foundation, Charlottesville, Va.

[21] Appl. No.: 42,193

[22] Filed: Apr. 21, 1987

Related U.S. Application Data

[63] Continuation-in-part of Ser. No. 741,601, Jun. 5, 1985, Pat. No. 4,741,998.

[51] Int. Cl.$^5$ ...................... A61K 39/395; C12N 5/20
[52] U.S. Cl. ................................ 530/387; 435/172.2; 435/240.27
[58] Field of Search ................. 435/68, 172.2, 240.27, 435/7.70, 810, 948; 935/95, 99, 100, 102-104, 108, 110; 436/548, 516, 808, 547, 543; 530/387, 388; 514/2

[56] References Cited

U.S. PATENT DOCUMENTS 4,511,661  4/1985  Goldberg ............................ 436/503

OTHER PUBLICATIONS

Shigeta, M. et al., "Sperm-Immobilizing Monoclonal Antibody to Human Seminal Plasma Antigens," *Clin. Exp. Immunol.*, 42(3):458–462, 1980, as cited in Biological Abstracts, accession #81:200013.

Ostrowski et al, "Purification and Cell-Free Synthesis of a Major Protein from Rat Seminal Vesicle Secretion", The Journal of Biological Chemistry, 254:383–390 (U.S.A. 1979).

Edwards et al., "Proteins of Human Semen: I. Two-Dimensional Mapping of Human Seminal Fluid", Clin Chem, 27:1335–1340 (U.S.A. 1981).

Balerna et al., "Low Molecular Weight Proteins in Human Seminal Plasma Electrophoretical Evidence of Their Vesicular Origin", Andrologia, 16:350–357 (U.S.A. 1983).

Hekman et al., "The Antigens of Human Seminal Plasma With Special Reference to Lactoferrin as a Spermatozoa-Coating Antigen", Fertility and Sterility, 20:312–323 (U.S.A. 1969).

Roberts et al., "Identification of Human Sperm-Coating Antigen", J. Reprod Fert, 18:347–350 (U.S.A. 1969).

Weil, "Antigens of the Seminal Plasma", J. Reprod Fert, Suppl. 2 25–34 (U.S.A. 1967).

Sensabaugh et al., "Isolation and Characterization of a Semen-Specific Protein for Human Seminal Plasma: A Potential New Marker for Semen Identification", Journal of Forsensic Sciences, 23:106–115 (U.S.A. 1978).

Koyarna et al., "Localization of Human Seminal Plasma No. 7 Antigen (Ferrisplan) in Accessory Glands of Male Genital Tract and Spermatozoa", Journal of Reproductive Immunology, 5:135–143 (U.S.A. 1983).

Abrescia et al., "Identification and Preliminary Characterization of a Sperm-Binding Protein in Normal Human Semen", J. Reprod Fert, 73:71–77 (U.S.A. 1985).

Isojima et al., "Purification of Human Seminal Plasma No. 7 Antigen by Immunoaffinity Chromatography on Bound Monoclonal Antibody", Clin Exp Immunol, 49:449–456 (U.S.A. 1982).

Herr et al., "Human Antisperm Monoclonal Antibodies Constructed Postvasectomy", Biol Reprod, 32 (3):695–712 (U.S.A. 1985), cited in Bio Abstract 80013306.

Uhlenbruck et al., "Unexpected Occurrence of the CA 19-9 Tumor Marker in Normal Human Seminal Plasma", Hoppe-Seyler's Z Physiol Chem, 365 (6):613–618 (U.S.A. 1984), cited in Bio Abstract 78079607.

Taylor et al., "Serum Prostatic Acid Phosphatase EC-3.1.3.2 Monoclonal Enzyme Linked Immunoassay ELISA Compared to Polyclonal Radioimmunoassay", Ann Clin Lab Sci, 14 (1):21–26 (U.S.A. 1984), cited in Bio Abstract 78004408.

Lad et al., "Identification of Structural and Secretory Lectin-Binding Glycoproteins of Normal and Cancerous Human Prostate", Biochim Biophys Acta, 791 (2):186–197 (U.S.A. 1984), cited in Bio Abstract 79078413.

Reynolds et al., "Production and Characterization of Monoclonal Antibodies to the Sperm Acrosome Stabilizing Factor Utilization for Purification and Molecular Analysis of Acrosome Stabilizing Factor", Biol Reprod, 30 (3):775–786 (U.S.A. 1984), cited in Bio Abstract 78039386.

Wolf et al., "Characterization of Human Sperm Surface Antigens with Monoclonal Antibodies", Biol Reprod, 29 (3):713–724 (U.S.A. 1983), cited in Bio Abstract 70063608.

Shigeta et al., "Sperm Immobilizing Monoclonal Antibody to Human Seminal Plasma Antigens", Clin Exp Immunol, 42 (3):458–462 (U.S.A. 1980), cited in Bio Abstract 7107005.

*Primary Examiner*—Margaret Moskowitz
*Assistant Examiner*—D. Bernstein
*Attorney, Agent, or Firm*—James C. Wray

[57] ABSTRACT

A monoclonal antibody MHS-5 which specifically binds to a seminal vesicle specific antigen, SVSA, wherein the seminal vesicle specific antigen is secreted by the principal cells of the seminal vesicle epithelium. The method for producing this monoclonal antibody is also disclosed.

2 Claims, 14 Drawing Sheets

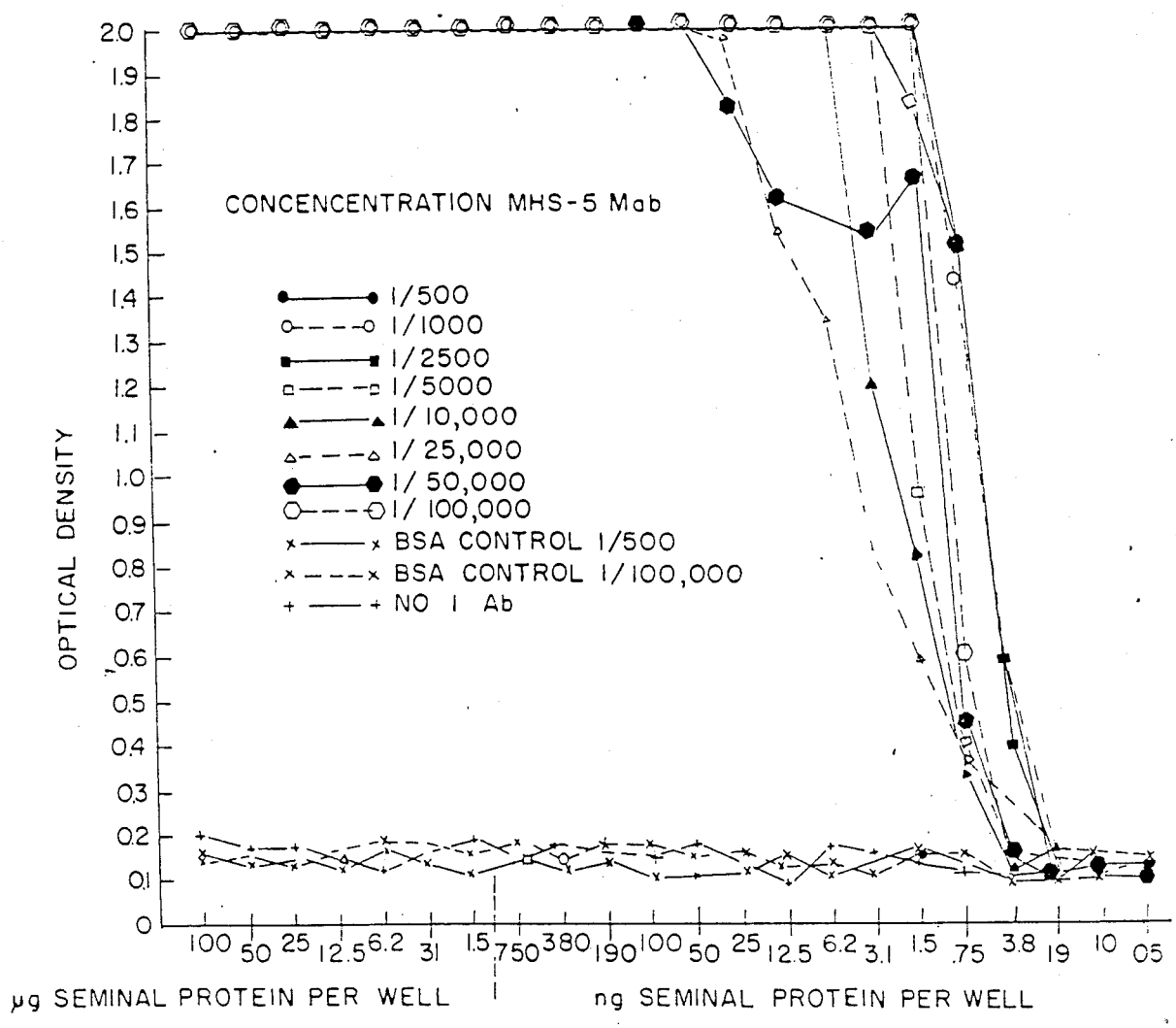

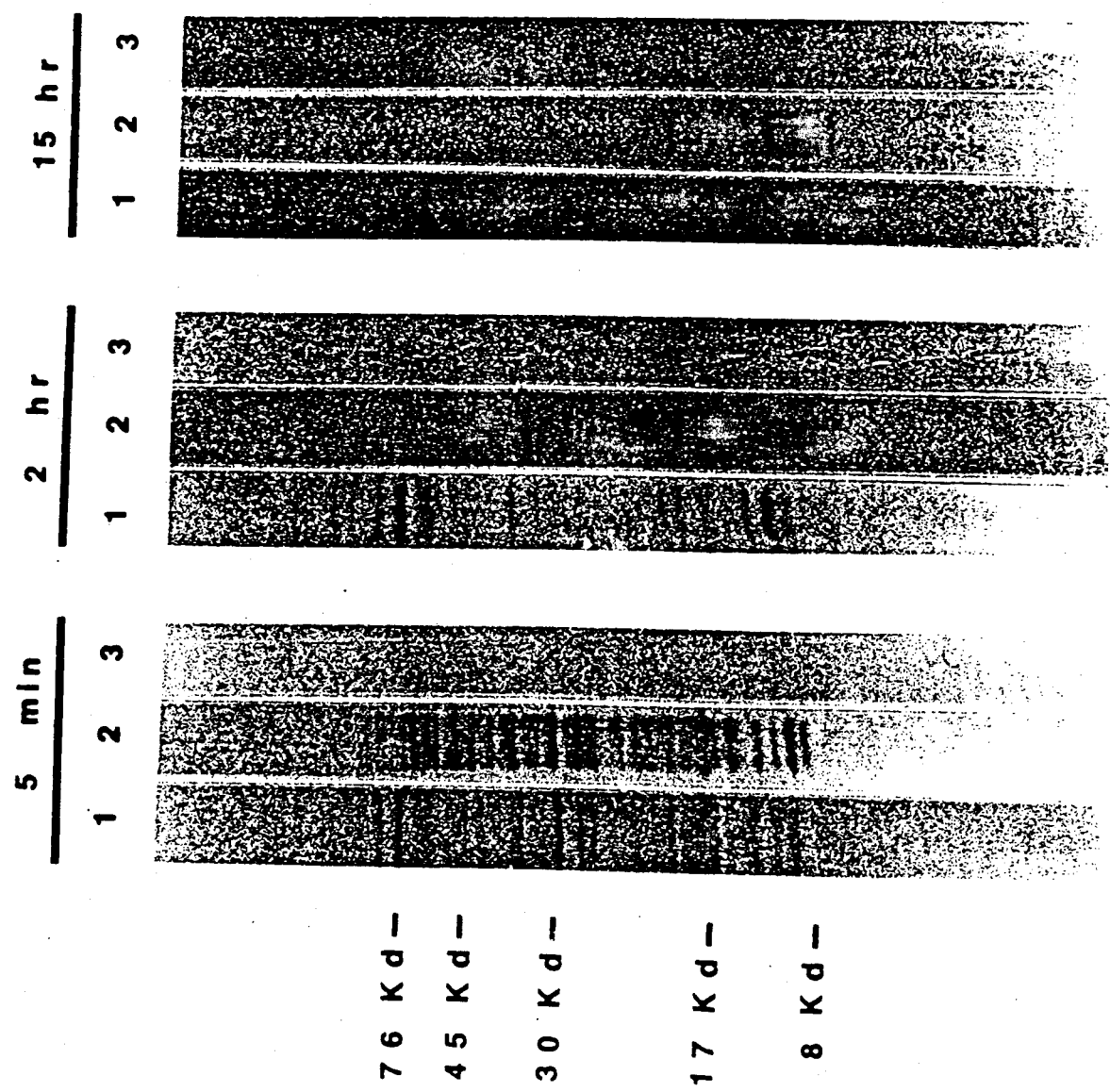

RATIO OF MHS-5 ANTIBODY AND SEMINAL PROTEIN

FIG.12A
FIG.12B
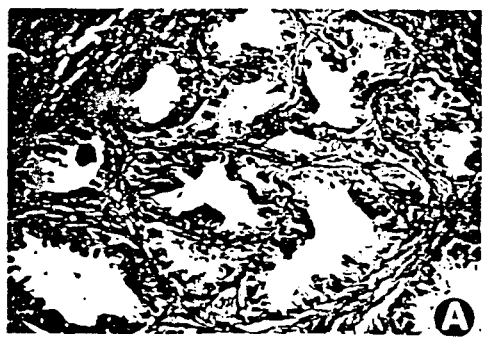
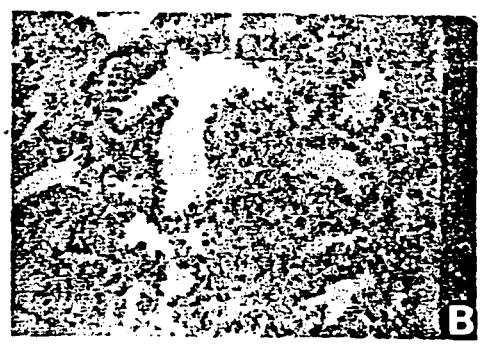
FIG.12C
FIG.12D

| SAMPLE (NUMBER TESTED) | NUMBER POSITIVE |
|---|---|
| HUMAN SEMEN (421) | 421 |
| HUMAN SERUM (15) | 0 |
| HUMAN SALIVA (16) | 0 |
| HUMAN AMNIOTIC FLUID (11) | 0 |
| HUMAN MILK (6) | 0 |
| HUMAN VAGINAL SECRETION (12) | 0 |
| HUMAN CERVICAL MUCUS (11) | 0 |
| HUMAN NASAL MUCUS (3) | 0 |
| HUMAN URINE - MALE (5) | 0 |
| HUMAN URINE - FEMALE (3) | 0 |
| HUMAN BILE (1) | 0 |
| HUMAN SWEAT (1) | 0 |
| RABBIT OVIDUCT FLUID (1) | 0 |
| RABBIT SEMEN (3) | 0 |
| SHEEP SEMEN (1) | 0 |
| DOG SEMEN (1) | 0 |
| PIG SEMEN (1) | 0 |
| RHESUS MONKEY SEMEN (1) | 0 |
| CAT SEMEN (1) | 0 |
| GOAT SEMEN (1) | 0 |
| SQUIRREL MONKEY SEMEN (1) | 0 |
| BULL SEMEN (1) | 0 |
| STALLION SEMEN (1) | 0 |
| RAT SEMINAL VESICLE FLUID (2) | 0 |
| MOUSE SEMINAL VESICLE FLUID (3) | 0 |
| GORILLA SEMEN (1) | 1 |
| CHIMPANZEE SEMEN (3) | 3 |
| ORANGUTAN SEMEN (1) | 1 |

| SAMPLE | MEAN ABSORBANCE (± SD) | SCORE (±) | MICROSCOPIC EVIDENCE OF SPERM |
|---|---|---|---|
| CONTROL | 0.174 (0.11) | − | |
| 1 | 1.303 (0.12) | + | + |
| 2 | >2000 (0) | + | + |
| 3 | 0.168 (0.008) | − | + |
| 4 | 0.146 (0.004) | − | − |
| 5 | >2.000 (0) | + | + |
| 6 | 0.152 (0.004) | − | − |
| 7 | 0.611 (0.041) | + | − |
| 8 | >2.000 (0) | + | + |
| 9 | 1.25 (0.016) | + | − |
| 10 | >2.000 (0) | + | − |
| 11 | 0.169 (0.003) | − | − |
| 12 | 0.143 (0.007) | − | − |
| 13 | >2.000 (0) | + | + |
| 14 | 0.144 (0.003) | − | − |
| 15 | 0.694 (0.038) | + | + |
| 16 | >2.000 (0) | + | − |
| 17 | 0.170 (0.002) | − | − |
| 18 | 0.158 (0.003) | − | − |
| 19 | 0.208 (0.013) | − | − |
| 20 | 1.902 (0.077) | + | − |
| 21 | >2.000 (0) | + | + |
| 22 | >2.000 (0) | + | + |
| 23 | 0.338 (0.008) | + | − |
| 24 | >2.000 (0) | + | − |
| 25 | 0.170 (0.007) | − | − |
| 26 | 0.163 (0.007) | − | − |
| 27 | 0.213 (0.0014) | + | + |
| 28 | 1.98 (0.02) | + | + |
| 29 | >2.000 (0) | + | + |
| 30 | >2.000 (0) | + | + |

MONOCLONAL ANTIBODY TO MHS-5; A NEW PROBE FOR SEXUAL ASSAULT ANALYSIS

This application is a continuation-in-part of Ser. No. 741,601, June 5, 1985, now U.S. Pat. No. 4,741,998 issued May 3, 1988.

BACKGROUND OF THE INVENTION

1. Field of the Invention

The present invention involves the cloning and isolation of a hybridoma secreting a monoclonal antibody to a highly conserved epitope on peptides that originate in the seminal vesicles.

2. Prior Art

More than 200 proteins ranging in mass from 10–100 kDa are observed when human seminal plasma is analyzed by high-resolution two-dimensional electrophoresis, Edwards et.al., *Proteins of Human Semen. I. Two-Dimensional Mapping of Human Seminal Fluid*, CLIN CHEM, 27(8):1335–40 (U.S.A. 1981). Many of the proteins of higher molecular mass in semen undergo proteolysis during liquefaction. Evidence obtained by massage of the prostate or seminal vesicles indicates that several seminal fluid proteins of low molecular mass in the 10-25 kDa range are of vesicular origin. The accessory sex glands, prostate and seminal vesicles contribute the majority of seminal plasma secretory proteins, with the prostate contributing from 15-30% of the ejaculate volume and the seminal vesicles accounting for 50-80%.

In the field of forensic science, attempts to corroborate an alleged rape by verifying the presence of semen in sexual-assault evidence have traditionally relied on microscopic evidence of sperm cells. Because some men lack spermatozoa in the ejaculate due to azoospermia or vasectomy, and because elution and recovery of sperm cells are often hampered by adherence to material evidence, tests for seminal fluid marker proteins, such as prostatic acid phosphates, prostate-specific antigen (P30), gamma glutamyl transpeptidase (GGT), choline, spermine, and lactate dehydrogenase (LDH) have been reported. Assays of choline, GGT, spermine, and LDH each have significant drawbacks and are not in general use.

In current forensic practice, the test for prostatic acid phosphatase is considered a presumptive, rather than a diagnostic, semen assay by most pathologists and forensic specialists. Acid phosphatase activity from endogenous vaginal sources or from the many plant materials that contain the enzyme may give false positive results. The enzyme also declines in activity upon storage at room temperature. For these reasons, when small amounts of semen may be present, as in eluates of dried semen stains from vaginal swabs or undergarments, the acid phosphatase activity cannot be attributed exclusively to semen.

Prostate-specific antigen (P30), a 32-kDA protein of prostatic origin, has been utilized by the forensic community as a semen marker since its introduction in 1978, Sensabaugh, *Isolation and Characterization of a Semen Specific Protein from Human Seminal Plasma: A Potential Marker for Semen Identification*, J FORENSIC SCI, 23:106-15 (U.S.A. 1978). Immunoassays based upon polyclonal antisera are generally employed, Graves et. al., *Post Coital Detection of a Male-Specific Semen Protein: Application to the Detection of Rape*, N ENGL J MED, 132:338-43 (U.S.A. 1985).

Because monoclonal-antibody-based immunoassays offer advantages over polyclonal immunoreagents, including their constant class and isotype, constant affinity, and availability in virtually unlimited supply, there is a need to develop monoclonal antibody probes useful for forensic application in semen identification.

SUMMARY OF THE INVENTION

The present invention involves the cloning and isolation of a hybridoma secreting a monoclonal antibody to a highly conserved epitope on peptides that originate in the seminal vesicles.

The MHS-5 monoclonal antibody recognizes a low-molecular-weight antigen present in liquefied semen of a large panel of human donors including semen obtained from vasectomized patients. This antigen localized by indirect immunofluorescence to the surface of ejaculated sperm over postacrosomal, midpiece, and tail regions. The antigen has been detected in no human biological fluid other than semen, nor is it found in semen of common domestic animals and monkeys. However, it is present in orangutan, gorilla, and chimpanzee semen. The antigenic epitope recognized by the monoclonal antibody has been shown by Western blots of proteins obtained from fresh ejaculates of vasectomized males to be located on peptides of a wide molecular weight range from 69 to 8 kD. After 15 hours of semen liquefaction, immuno-reactive peptides of higher molecular weight were undetectable in semen, while lower molecular weight peptides from 8 to 21 kD retained antigenicity. Three peptides of 10, 11.9 and 13.7 kD were the most reactive species in semen liquefied for 15 hours.

Antibody binding to the antigen has been found to persist in mixtures of semen and vaginal secretion maintained at 37° C. for 4 hr, attesting to the stability of the antigenic epitope in the female tract. Because this protein antigen is present in semen from all tested donors, it has been proposed as a new forensic marker for the management of sexual assault casework using assay system based on the MHS-5 monoclonal antibody probe.

The MHS-5 antigen is localized in human seminal vesicle epithelial cells and can be reconstituted on the surface of epididymal sperm by mixing such sperm with semen from vasectomized men or with the contents of the seminal vesicle lumen. This suggests that the MHS-5 monoclonal antibody recognizes a sperm-coating antigen that is a secretory product of the human seminal vesicle epithelium.

These and further and other objects and features of the invention are apparent in the disclosure, which includes the above and ongoing written specification, including the claims and the drawings.

BRIEF DESCRIPTION OF THE DRAWINGS

FIG. 2 shows a graph depicting results from enzyme linked immunosorption assay (ELISA) wherein seminal fluid protein concentrations and dilutions of the monoclonal antibody were varied. MSH-5 binding to seminal fluid is compared to binding to bovine serum albumin.

FIG. 8 shows a photograph of an immunoblot identification of polypeptides reacting with monoclonal antibody MHS-5 during the course of semen liquefaction. The nitrocellulose strips contained proteins electrophorised after 5 minutes, 2 hours, or 15 hours of semen liquefaction.

FIGS. 12A-D are photomicrographs displaying human seminal vesicles sections after immunolocalization employing the MHS-5 monoclonal antibody and the avidin-biotin-peroxidase technique. Specifically, FIG. 12A shows a hematoxylin and eosin stain of 6-μm-thick paraffin embedded material, formaldehyde fixation; FIG. 12B shows a tissue section incubated with absorbed monoclonal antibody MHS-5; FIG. 12C shows immunolocalization of the MHS-5 antigen in the seminal vesicle epithelium; and FIG. 12D shows a high-magnification-like micrograph demonstrating immunolocalization of the MHS-5 antigen within the cytoplasm of the principal cells.

FIG. 14 is a table of biological fluids which were tested for the MHS-5 antigen by the ELISA method.

FIG. 15 is a table indicating results from analysis of eluants of forensic stains from sexual assaults which were tested for the MHS-5 antigen by the ELISA method.

DETAILED DESCRIPTION OF THE INVENTION

Figure 1A:
FIG. 1 shows human sperm before and after being stained with the MHS-5 monoclonal antibody (FIG. 1B). The differential interference contrasts images of the spermatozoa are presented in FIG. 1A.

A panel of hybridomas secreting antisperm monoclonal antibodies was generated by conventional procedures, Galfre et. al., *Antibodies to Major Histocomoatibility Antigens Produced by Hybrid Cell Lines*, NATURE, 266:550-52 (U.S.A. 1977). Splenocytes from BALB/c female mice, immunized four times with $10^7$ washed human sperm (suspended in incomplete Freund's adjuvant), were fused with the myeloma cell line SP2/0, Shulman et.al., *A Better Cell Line for Making Hybridomas Secretion Specific Antibodies*, NATURE, 276:269-70 (U.S.A. 1978). The immunizing sperm were all obtained from blood type O donors.

An enzyme-linked immunosorbant assay using Immulon II microtiter plates (Dynatech Laboratories, Alexandria, VA) was developed to test for the presence of the MHS-5 antigen in biological fluids and on sperm. Briefly, after protein determination, Bradford, *A Rapid and Sensitive Method for Ouantitation of Microgram Quantities of Protein Utilizing the Principle of Protein Dye Binding*, ANAL BIOCHEM, 72:248-54 (U.S.A. 1976), 100 μl of protein from various biological fluids were coated at varying concentrations onto microtiter wells in a carbonate-bicarbonate buffer, pH 9.2, for 2 hours at 37.C. Plates were blocked with 0.1% Tween/phosphate-buffered saline (PBS), pH 7.2, for 30 minutes. Then 100 μl per well of monoclonal antibody MHS-5 ascites, diluted 1/100,000 in PBSTween, 1% bovine serum albumin (BSA) was incubated with the antigen for 1 hour (equivalent of 27 ng IgG per well). Peroxidase-labeled goat antimouse IgG (Hyclone, Logan UT) at a dilution of 1/1,000 in PBS-Tween, 1% BSA, was incubated for 30 minutes as a secondary antibody. The substrate 2,2-azino-di-(3-ethylbenzthiazoline sulfonic acid) (ABTS) was used to develop a colored reaction, the optical density of which was read on a Microtiter Multiscan MC (Flow Laboratories, McLean, VA) after 30 minutes.

Hybridomas that elicited positive binding to sperm were expanded and cloned by limiting dilution. Hybridomas were then screened by ELISA for binding to (1) normal healthy male seminal fluids, cleared of sperm by centrifugation, and (2) seminal fluids obtained from vasectomized men. Seminal fluid proteins were coated, 1 μg/well, for 1 h with subsequent ELISA steps performed as above. The immunoglobulin class of the monoclonal antibodies was determined on culture supernatants using ELISA assay employing class-specific secondary antibodies (Hyclone) to mouse immunoglobulins.

Ascites fluids were produced and assayed for immunoglobulin (Ig) concentration by an ELISA patterned after the published procedure for human Ig, Herr et.al., *Human Antisperm Monoclonal Antibodies Constructed Post-Vasectomy*, BIOL REPROD, 32:695-711 (U.S.A. 1985). Working dilutions of monoclonal antibody ascites for ELISA were determined by titration of ascites against normal seminal fluid coated onto microtiter plates over the range 100 μg/well-0.05 ng/well.

Human milk, saliva, serum, amniotic fluid, nasal mucus, and urine were obtained from donors and frozen at −70° C. within 15 minutes of receipt. Vaginal secretions and cervical mucus were obtained on sterile swabs during routine pelvic examinations. Semen from common domestic animals and monkeys were gifts of the FBI (Quantico, VA) and Dr. Eugene Oliphant (University of Virginia). Semen samples from Pongid primates were obtained from the Yerkes Primate Center (Atlanta, GA). Protein was determined by the method of Bradford, *A Rapid and Sensitive Method for Quantitation of Microgram Quantities of Protein Utilizing the Principle of Protein Dye Binding*, ANAL BIOCHEM, 72:248-54 (U.S.A. 1976). Samples were coated over varying protein concentrations (50 µg/well-0.1 µg/well) in carbonate bicarbonate buffer for ELISA.

Human seminal vesicle, prostate, testis, epididymis, kidney, liver, spleen, and pancreas were obtained from 10 cadavers within 6 h of death and homogenized in carbonate bicarbonate buffer, pH 9.2, using a Precision Scientific (Fisher Scientific, Richmond, VA) tissue homogenizer. The homogenates were centrifuges for 10 minutes at 500 x g to pellet particulate material, and the soluble proteins were precipitated using cold acetone in a 10:1 ratio. A pellet of the precipitated proteins was obtained after 10 minutes of centrifugation at $500 \times g$ and was resuspended in carbonate bicarbonate buffer. Samples for ELISA were coated onto microtiter wells at 100 µg/well-100 ng/well. Purified prostatespecific antigen, P30, was purchased from T. M. Chu (Roswell Park Memorial Institute, Buffalo, NY), and purified lactoferrin was purchased from Sigma Chemical Company (St. Louis, MO). These samples were coated at 20 µg/well for ELISA.

To assay binding of the monoclonal to various sperm populations, epididymal sperm were obtained at vasovasostomy (Patient #1) and orchiectomy (Patient #2), washed 3 times, and coated for ELISA )$10^5$ sperm/well). Sperm from normal donors ($10^5$ sperm/well), seminal fluid from vasectomized donors (100 µg/well), and protein from seminal vesicles obtained at autopsy (100µg/well) were used as positive controls, with BSA (100µg/well) as the negative control. Sperm-coated wells to which no primary antibody was added were used to assess nonspecific binding of the secondary antibody.

Seminal fluid and cervical or vaginal fluids of known protein concentration were mixed in varying ratios from 50/50 to 0/100 (seminal/cervical). After incubation at 37° C. for 4 hours, 2.0 µg of each mixture was coated in microtiter wells and ELISA performed as above. BSA-coated wells served as controls.

Simulated forensic evidence was generated by drying ejaculates from 15 normal donors onto cotton cloth that was stored at room temperature for one week. Thirty cloth samples from actual forensic casework were obtained from the FBI after storage at room temperature for one to five months. The samples had previously been microscopically examined for the presence of sperm cells and were assayed blind. Protein from 1-cm squares cut from both the simulated and actual evidence were eluted in PBS, pH 7.2, and tested for antibody reactivity by ELISA after protein determination. Ten micrograms of eluant protein was used to coat microtiter wells.

Indirect immunofluorescent localization of the MHS-5 antigen on ejaculated human spermatozoa was performed according to the methods of Herr et.al. (1985) and employed FITC-goat antimouse Ig (Cappel Laboratories, Cochranville, PA), 1:150 in PBS. Controls consisted of PBS, preimmune mouse sera, SP2/0 culture supernatants, and postimmune mouse sera.

Seminal fluid from vasectomized donors was allowed to liquefy at room temperature for 15 hours. Two hundred microliter aliquots were removed at 5 minutes, 2 hours, and 15 hours and diluted 1:1 with 4% SDS. The protein concentrations were determined by absorbance at 280 nm and diluted in buffer (50 mM Tris-HCl, pH 6.8, 1.0% SDS, 30.0% glycerol, 0.2 mM phenylmethylsulfonyl fluoride [PMSF]) to 1 mg/ml and heated in boiling water for 5 minutes. Mercaptoethanol was then added to a final concentration of 1.0%. Twenty micrograms of sample were loaded into each lane of a 15% polyacrylamide gel (16 cm in length), electrophoresed at 5 mA constant current, and subsequently electrotransferred to nitrocellulose paper (0.2 µm) at 100 mA for 18 hours. Portions of the nitrocellulose were cut and stained with 0.1% amido black. Experimental strips were blocked in 5% nonfat dry milk at 20° C. for 30 minutes and then incubated in either the purified MHS-5 antibody or a control monoclonal antibody (Mab-3, $IgG_1$) both diluted in 0.01 M PBS/0.5% Tween 20/0.1% BSA pH 7.2 to a concentration of 4 µg/ml. The strips were washed 3 times in the above-mentioned buffer and subsequently incubated with peroxidase conjugated goat antimouse Ig (Hyclone, 1/10,000) for 1 hour at room temperature. The strips were again washed and identification of antigenic polypeptides completed by incubating the strips in 0.04% diaminobenzidine/0.015% $H_2O_2$ in PBS pH 7.2.

Figure 1B:
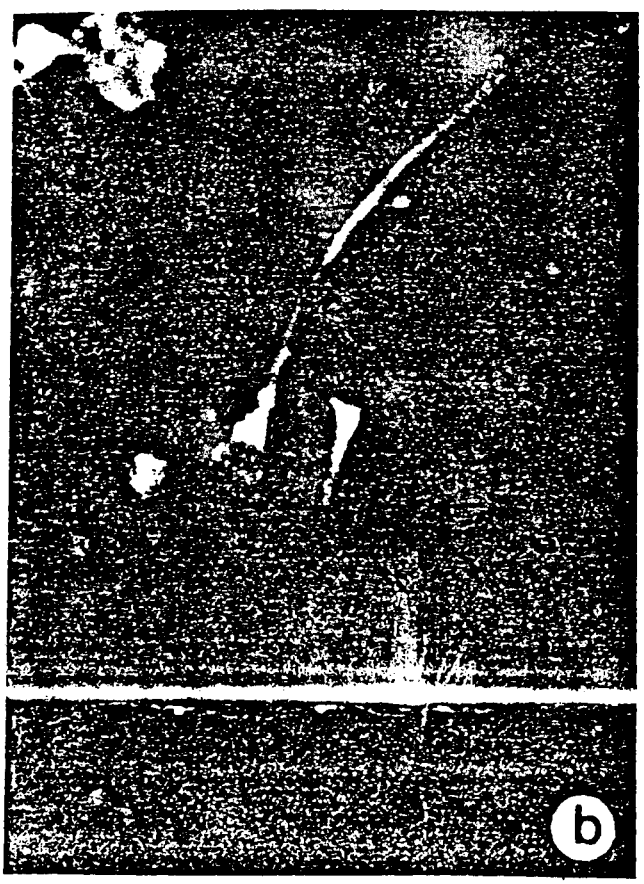

Twenty-five hybridoma lines, which were found by ELISA to secrete antibody to human sperm from blood type O donors, yielded 9 hybridoma antibodies which bound only to sperm-free seminal fluid and five monoclonal antibodies reactive with seminal fluid from vasectomized men. One of these five hybridomas, clone MHS-5 (mouse anti-human sperm-5), produced an antibody of the $IgG_1$ subclass that bound to seminal fluids from all 400 normal donors tested and to the 21 semen samples from vasectomized men. No ejaculate was found that did not test positive for the MHS-5 antigen. Ejaculated spermatozoa from normal men were incubated with the MHS-5 antibody followed by a fluorescent antimouse IgG secondary antibody and examined microscopically for localization of the MHS-5 antigen. Intense fluorescence of the postacrosomal, midpiece, and tail regions, with lesser staining of the acrosome (FIG. 1B), was observed. This pattern occurred in 90% of the sperm from each donor (N=5) and was not altered by methanol fixation. A polyclonal mouse antisperm sera from an immune animal used to perform the hybridoma fusions was used as a positive control giving uniform fluorescence of the sperm. Negative controls showed no immunofluorescence of the sperm.

The MHS-5 monoclonal antibody ascites was titered against human seminal fluid using the ELISA assay in which concentrations of seminal fluid proteins coated onto microtiter plates and the monoclonal antibody were varied (100 µg/well-0.05 ng/well) (FIG. (2). All dilutions of the monoclonal antibody to 1/100,000 gave optical density (OD) readings of 2 or greater (the upper limit of the Microtiter Multiscan) on plates coated with solutions containing as little as 50 ng seminal protein/well. Negative control plates coated with BSA over the same concentration range and plates not coated with primary antibody, to assess the nonspecific binding of the secondary antibody, gave OD readings from 0.1 to 0.2 Using the criterion of OD readings twice the BSA-coated control-well readings as the standard for a positive identification (approximately four standard deviations above the mean of the BSA controls), the ELISA assay was sensitive enough to identify semen as low as 0.75 ng seminal fluid protein/well at a 1/100,000 dilution of the monoclonal ascites. At this dilution each well received 27 ng of the monoclonal probe.

Figure 3:
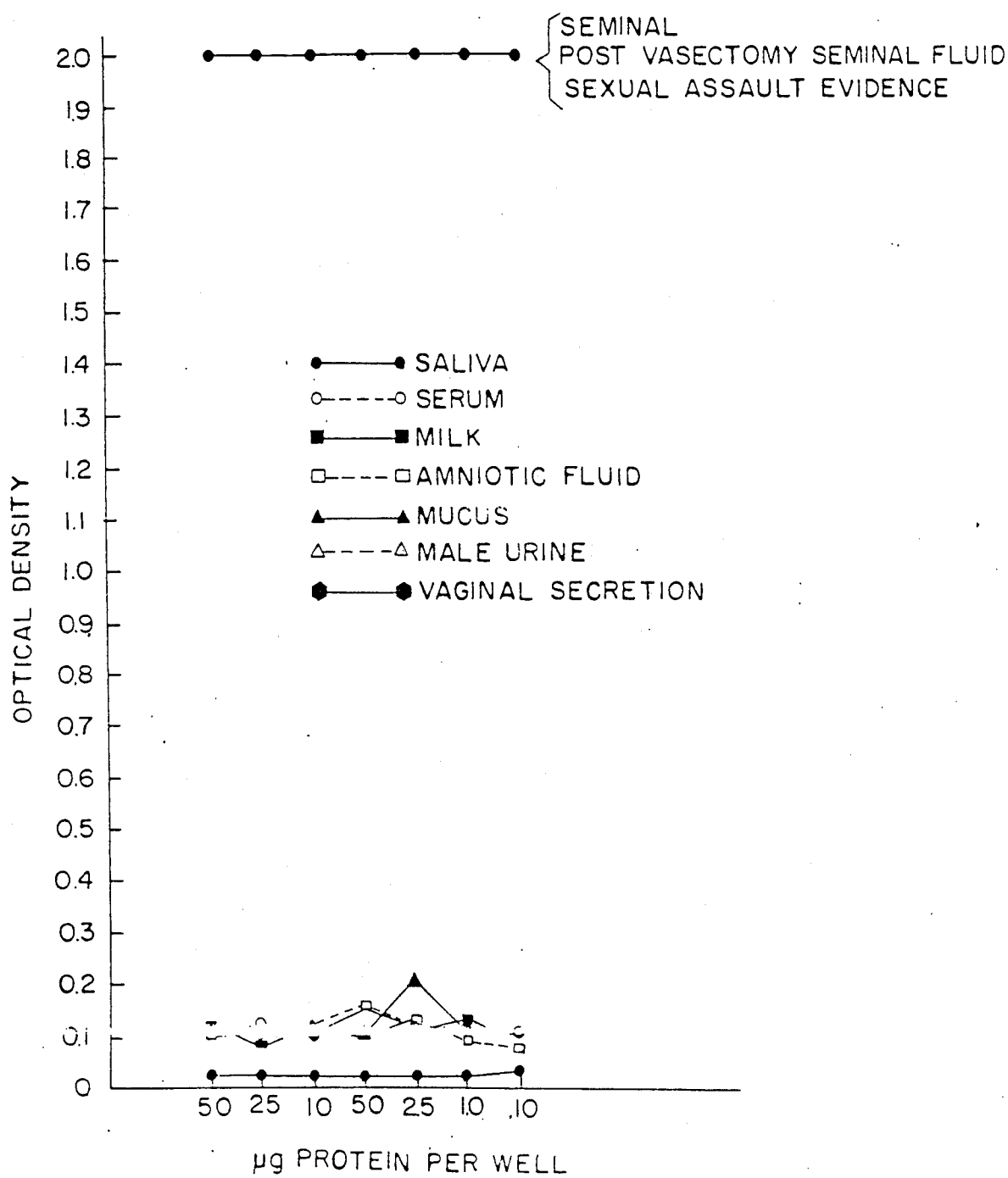
FIG. 3 shows a graph depicting results from ELISA testing of seminal fluid, post vasectomy seminal fluid, sexual assault evidence and various biological fluids for the presence of the MHS-5 antigen. The MHS-5 antigen is not found in any biological fluid other than semen.

ELISA was used to determine whether the epitope recognized by the monoclonal antibody was present in any other human biological fluid. FIG. 3 shows the reactivity of MHS-5 with human seminal fluid, compared to several other human biological fluids coated onto microtiter plates at varying concentrations of protein. The MHS-5 ascites antibody was employed at a 1/100,000 dilution. As can be seen in FIG. 3, other biological fluids tested gave OD readings at the background levels typical of BSA controls (FIG. 2), while MHS-5 Mab gave OD readings of 2 or greater on wells coated with seminal fluid from normal and postvasectomy donors. Of particular forensic interest is the finding that the MHS-5 antigen could not be detected in human serum, saliva, vaginal protein, cervical mucus, or human milk. FIG. 14 summarizes the biological fluids examined by ELISA for the presence of the MHS-5 antigen. The MHS-5 antigen has been undetectable in any other human biological fluid tested to date.

Semen from several common domestic animals were examined and found to lack the MHS-5 antigen (FIG. 14). Although only a few nonhuman primate semen samples have been tested, the MHS-5 antigen was not detected in rhesus (*Macca mulatta*) or squirrel monkey (*Saimiri sciureus*) but was found in gorilla, chimpanzee, and orangutan semen (FIG. 14). The levels of the antigen in these Pongidae species appears to be comparable to levels in human semen (data not shown).

Figure 4:
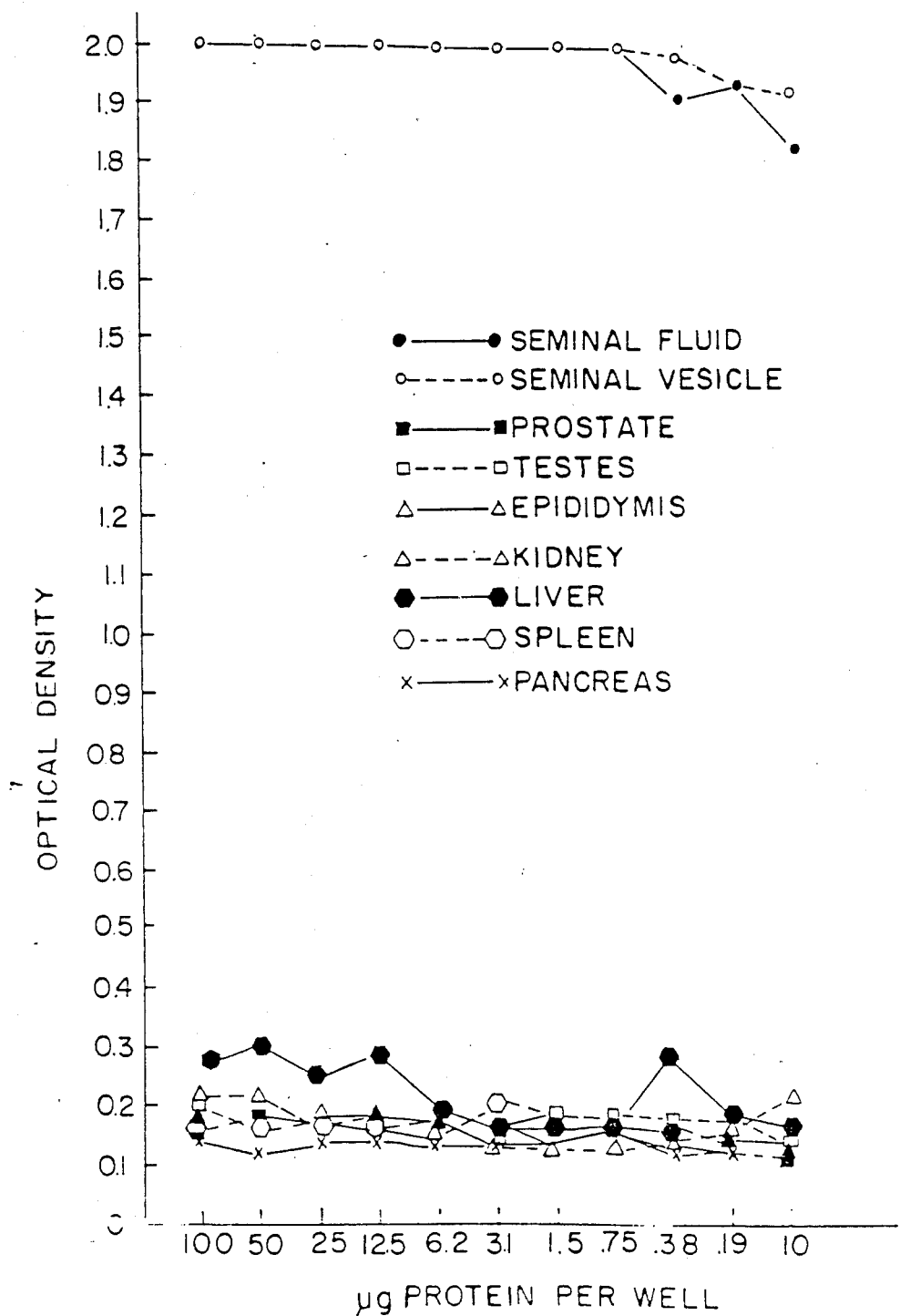
FIG. 4 is a graph depicting results from ELISA testing seminal fluid from normal donors and tissue homogenates from seminal vesicle, prostate, testes, epididymis, kidney, liver, spleen and pancreas. The MHS-5 antigen was found to localize in the seminal vesicles.

Homogenates of various reproductive tract organs obtained at autopsy were assayed to identify the tissue origin for the MHS-5 seminal antigen (FIG. 4). Seminal vesicle homogenates gave OD readings of 2, whereas homogenates of other reproductive tract organs gave OD readings similar to the background control values (FIG. 2), indicating that the MHS-5 antigen is located in the seminal vesicles. Homogenates of kidney, pancreas, spleen, and liver also gave background OD readings, indicating that the MHS-5 antigen was absent in these tissues.

Figure 5:
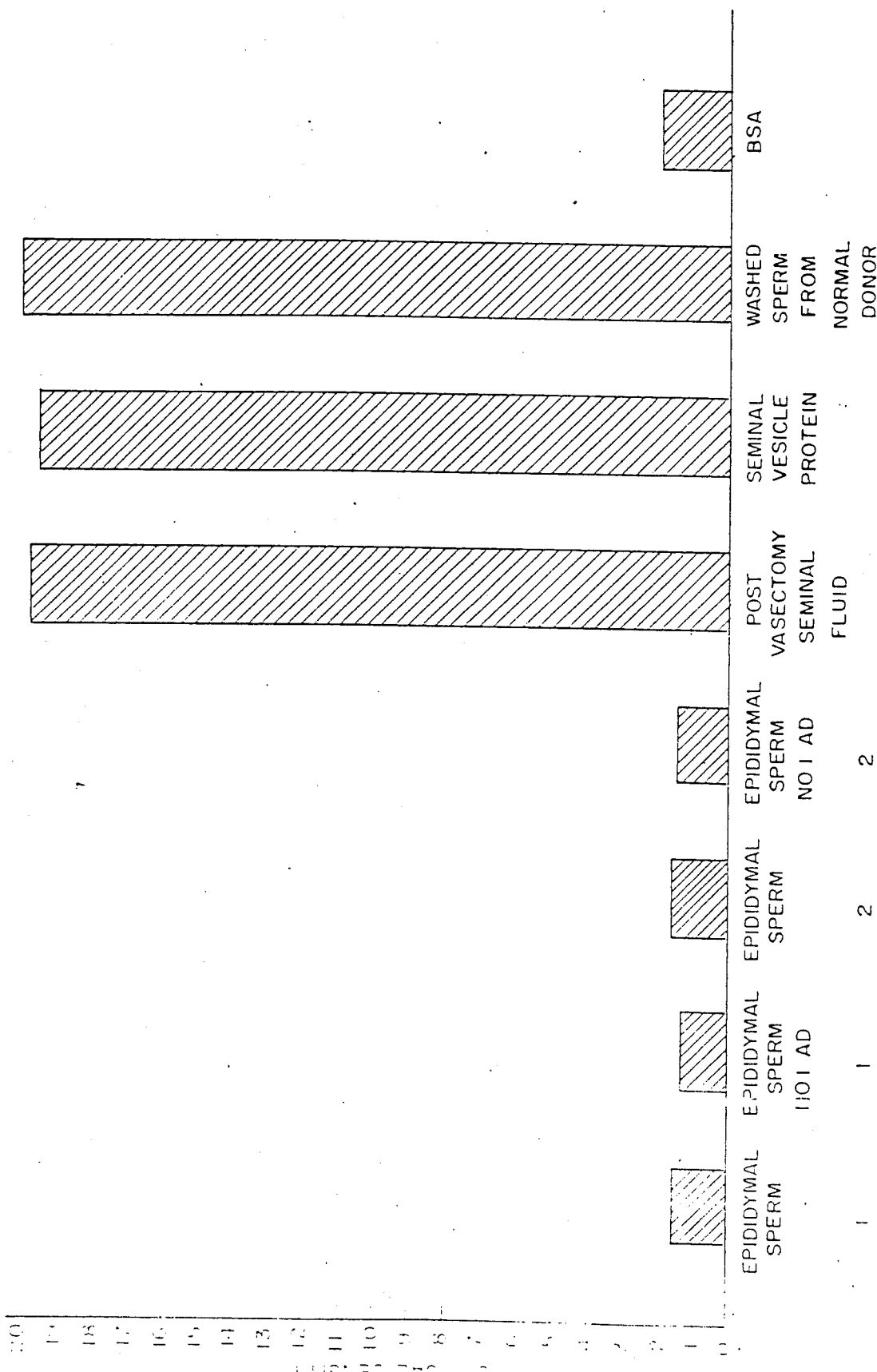
FIG. 5 is a bar graph depicting results from ELISA testing for the presence of the MHS-5 antigen on epididymal sperm obtained by vasovasostomy and orchiectomy. Although present on ejaculated sperm the MHS-5 antigen is absent on epididymal sperm.

Epididymal sperm (cauda) obtained from one patient at the time of vasovasotomy and another patient during orchiectomy, were plated onto microtiter plates at the same concentration as ejaculated sperm ($10^5$ well), and the binding of the MHS-5 monoclonal to the two populations of sperm was compared. Epididymal sperm (as well as the epididymal homogenate notes above) gave OD readings similar to the BSA-coated control wells, indicating that epididymal sperm lack the MHS-5 epitope; the ejaculated sperm gave high OD readings, indicating the presence of the MHS-5 antigen (FIG. 5).

Figures 6, 7:
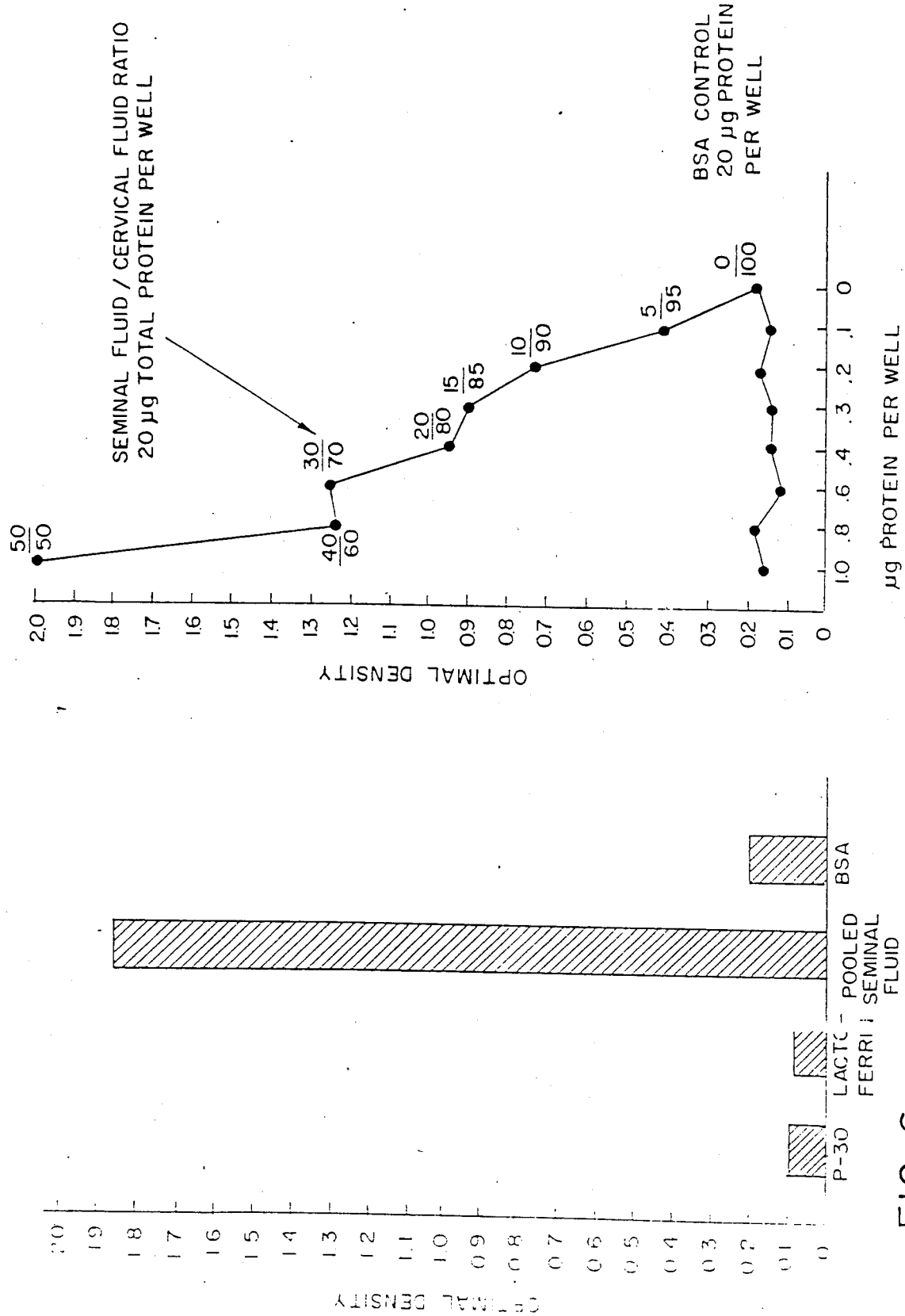
FIG. 6 is a bar graph depicting results from ELISA testing to determine if the epitope recognized by the monoclonal antibody to MHS-5 antigen is present on p30 (prostate specific antigen) or lactoferrin. The monoclonal antibody MHS-5 does not cross-react with the previously described seminal fluid proteins.
FIG. 7 is a graph depicting results from ELISA testing for the MHS-5 antigen in mixtures of seminal fluid and cervical fluid. The MHS-5 antigen is still detectable in mixture of semen with cervical fluid.

Earlier work demonstrated that the protein lactoferrin is a sperm-coating antigen of human seminal vesicle origin. To determine if the MHS-5 antibody exhibited any cross-reactivity with lactoferrin or with the well known prostate marker P30, a cross-reactivity study of the MHS-5 probe with purified P30 (prostate-specific antigen) and human milk lactoferrin was made. No cross-reactivity of the MHS-5 monoclonal antibody and these previously characterized seminal proteins was observed (FIG. 6).

In order to discover if the MHS-5 antigen was masked or rapidly degraded in the presence of vaginal or cervical proteins, seminal proteins were mixed with vaginal secretion and cervical mucus and then tested for the presence of the MHS-5 antigen. A pool of vaginal and cervical protein from 10 individuals was made. Various ratios of seminal protein to vaginal/cervical protein were prepared, allowed to incubate together for 4 hours at 37° C., and then analyzed by ELISA. A typical result from these experiments is shown in FIG. 7. In such mixtures, after 4 hours of incubation it was possible to detect as little as 0.1 μg of total seminal protein in 1.9 μg of vaginal protein (19:1 ratio).

Semen has been subjected to several treatments in an attempt to alter antibody binding on ELISA. The following treatments of human semen have not altered the ability of the MHS-5 monoclonal (1/100,000 ascites) to recognize seminal-fluid-coated plates (10μg/well): 1) heating at 65° C. or boiling at 100.C for 2 hours; (2) treatment at pH 1.8 for 12 hours; 3) freezing in liquid nitrogen for 16 hours. Incubation of semen in 5 mg/ml pepsin for 12 hours at pH 1.8 eliminated binding of the MHS-5 antibody to its epitope.

Proteins from the semen of vasectomized men after semen liquefaction for 5 minutes, 2 hours, or 15 hours were separated by SDS-PAGE and electrotransferred to nitrocellulose for immunolocalization (FIG. 8). Lane 1 demonstrates the total complement of seminal fluid proteins stained by amido black on the nitrocellulose at each of the time intervals. Lane 2 at each time period contains protein bands that reacted with monoclonal MHS-5. Lane 3 are nitrocellulose strips incubated in another monoclonal antibody (Mab-3 to acrosome-stabilizing factor) at the same antibody concentration as MHS-5 and processed identically. At 5 minutes after ejaculation, multiple immunoreactive bands were present between 8 and 69 kDa. The immunoblot detected many bands not stained with amido black. After 2 hours of liquefaction, higher molecular-mass immunoreactive bands were not present, although protein bands were present and stained with amido black in the higher molecular-mass range. Immunoreactive bands were found between 8 and 43 kDa after 2 hours of liquefaction.

After 15 hours of liquefaction, the immunoreactive bands were found predominantly in the lower molecular-mass range. Three major reactive bands were identified (arrows) with molecular masses of 10.0, 11.9, 13.7 kDa. Bands of lesser intensity were found to have molecular masses of 8.2, 14.7, 15.9, and 21.2 kDa. When the immunoreactive peptides after 15 hours of liquefaction (Lane 2) are compared to the protein stain, nonimmunoreactive higher-molecular-mass peptides are evident (Lane 1).

All of the saline eluants from simulated sexual assault evidence samples tested positive for semen using the MHS-5 probe. Of 30 samples from actual forensic casework, semen was positively identified in 19 by ELISA (FIG. 15). Of these 19 samples positive for the MHS-5 antigen, spermatozoa had been microscopically confirmed on 13. Eleven samples tested negative for the MHS-5 antigen, and spermatozoa were found microscopically in one of these samples (#3).

The MHS-5 antibody and the MHS-5 antigen are proposed as a novel semen probe and semen marker antigen on the basis of the following observations: (1) The MHS-5 epitope was found conserved in the semen of all donors tested (421), including vasectomized men.

(2) No cross-reactivity was observed with any other human biological fluid or with the semen of common domestic animals. (3) A sensitive, inexpensive enzyme-linked immunosorption assay (ELISA) was developed that gives a positive identification of semen with as little as 0.75 ng seminal fluid protein present. (4) The antigen was not masked or eliminated in vaginal fluids and was detected in mixtures of semen and vaginal fluid incubated together at body temperature for 4 hours. (5) The antigen originated in the seminal vesicles, the major contributor of secretions to the ejaculate. (6) The antigenic epitope was thermo-stable and (7) was detected in forensic casework collected several months previously.

The MHS-5 antigen was not found on epididymal sperm but was present on washed ejaculated sperm, qualifying it as a "spermcoating antigen". Weil first demonstrated an antigen, termed "sperm-coating antigen", that originated in the human seminal vesicles and coated the human sperm surface during ejaculation. Weil, *Antigens of the Seminal Plasma*, J REPROD FERTIL (SUPPL), 2:25-34 (U.S.A. 1967). At least six sperm-coating antigens have since been identified in human seminal plasma. Only two of these antigens, lactoferrin, also known as scafferin, and the seminal plasma No. 7 antigen (ferrisplan) have been shown to originate in the human seminal vesicles. These proteins share antigenic cross-reactivity with similar proteins in human milk. Several considerations suggest that the MHS-5 antigen is a unique seminal vesicle protein distinct from the sperm-coating antigens lactoferrin and No. 7 antigen. Human seminal lactoferrin, when electrophoresed in a Laemmli system similar to that used in this study, has an apparent molecular mass of 80 kDa, whereas seminal plasma No. 7 antigen, when electrophoresed under reducing conditions, has a molecular mass of 15 kDa. Thus, neither of these previously described sperm-coating antigens of seminal vesicle origin has the same molecular mass as the predominate 1013 kDa immunoreactive peptides recognized on Western blots after 15 hours of liquefaction by the MHS-5 monoclonal. Further, antisera produced to lactoferrin or to seminal plasma No. 7 antigen have shown cross-reactivity with similar proteins in human milk. The MHS-5 monoclonal antibody gave background OD readings on all human milk samples tested and failed to bind to purified milk lactoferrin.

In a recent report, a protein immunologically related to a rat seminal vesicle protein, SVS-IV, was detected in human seminal fluid, Abrescia et.al., *Identification and Preliminary Characterization of a Sperm-Binding Protein in Normal Human Semen*. J REPROD FERTIL, 73:71-77 (U.S.A. 1985). SVS-IV has been reported to have a molecular mass of 17 kDa, considerably higher than that of the major protein group recognized by the MHS-5 monoclonal antibody. Wahlstrom et.al. discovered placental protein 5 (PP5) in the seminal plasma and used and polyclonal rabbit anti-PP5 antiserum and an immunoperoxidase staining technique to localize PP5 to the seminal vesicle epithelium. PP5 does not function as a sperm-coating antigen, Wahlstrom et.al., *Immunohistochemical Demonstration of Placental Protein 5 (PP5)-like Material in the Seminal Vesicle and the Amoullar Part of the VBas Deferens*, LIFE SCI, 31:2723-25 (U.S.A. 1982). Wahlstrom and Ranta also demonstrated that prolactin (also a noncoating antigen) is present in human seminal vesicle secretion. Prolactin localizes to a perivascular cell population located in the venous plexuses between the folds of the seminal vesicle walls and not to seminal vesicle epithelial cells, Wahlstrom et. al., *Accumulation of Prolactin in Human Seminal Vesicles As Revealed By Immunohistochemical Studies*, FERTIL STERIL, 40:545-48 U.S.A. IgB3). The molecular mass of prolactin is 22 kDa; and that of PP5 is 36 kDa. Thus, when compared to previously names human seminal vesicle antigens (both sperm-coating and non-sperm-coating), the component recognized by the MHS-5 monoclonal antibody in liquefied semen appears to represent a unique sperm-coating antigen of seminal vesicle origin.

Analyses of human semen by two-dimensional gels and by one-dimensional SDS-PAGE of split ejaculate fractions have shown that seminal fluid contains several families of major proteins in the 0-25 kDa range. These proteins are found in the final or seminal vesicle portion of the split ejaculate and show changes in molecular mass during semen liquefaction. The MHS-5 monoclonal provides a probe for several of these seminal vesicle peptides previously lacking an immunological identity.

We have demonstrated the MHS-5 epitope to be located on peptides that range from 8-69 kDa in ejaculates allowed to liquefy for 5 minutes from 4 individuals (all data not shown). After 15 hours of semen liquefaction, higher molecular-mass immunoreactive peptides disappear and a group of low molecularmass immunoreactive peptides from 8-21 kDa persist in semen after this liquefaction period. Peptides of 10-13.9 kDa are the major immunoreactive species. Further studies, employing several vasectomized donors, that carry the liquefaction period out past 15 hours are currently underway to determine which peptides in the 8-17-kDa range may represent a stable form of the antigen.

An epitope of this kind that shows molecular-mass changes during semen liquefaction might be explained by several models, of which we note two: (1) The multiple immunoreactive proteins seen in the fresh ejaculate may be unrelated except for sharing a common epitope. The action of endopeptidases during liquefaction may clip peptides of varying length, inclusive of the epitope, from their larger parent molecules to result in a group of lower molecular-mass peptides exhibiting some microheterogeneity of mass. (2) Semen coagulation in rodents involves polymerization of seminal vesicle secretions by transglutaminases of prostatic origin. The MHS-5 epitope may occur on a molecule that covalently binds to itself or to other seminal proteins as accessory gland secretions are mixed during ejaculation. After liquefaction, the observed immunoreactive peptides (8017 kDa) represent the epitope still bound to seminal fluid proteins that have undergone proteolytic cleavage, resulting in variable molecular masses. To our knowledge, the seminal vesicle secretions that are substrates for transglutaminase-mediated coagulation of human semen are uncharacterized.

Boiling seminal fluid for 2 hours or freezing in liquid nitrogen before coating for ELISA did not decrease the binding of the MHS-5 monoclonal antibody when compared to untreated seminal fluid. Pepsin treatment of seminal fluid before binding to the plate eliminated subsequent recognition by the MHS-5 monoclonal antibody. Because pepsin initiates hydrolysis of proteins at peptide bonds involving the carboxyl group of aromatic amino acids, but does not degrade carbohydrate that might be associated with a protein, these results suggest that the epitope recognized by the MHS-5 monoclonal is possibly a thermostable, proteinaceous domain. However, pepsin may degrade the MHS-5 antigen to such an extent that binding to the plate is prevented. If this is the case, the possibility that MHS-5 recognizes a carbohydrat-associated epitope cannot be excluded.

By ELISA the MHS-5 monoclonal antibody did not bind to purified prostate specific antigen (PSA or P30). This finding suggests that MHS-5 is directed to a seminal fluid marker protein distinct from the prostatic semen marker P30. Future management of forensic casework could employ immunological probes for both seminal markers. Because the MHS-5 monoclonal bound to ejaculated sperm both on ELISA assay and by immunofluorescence, the antibody may be useful as a probe for spermatozoa on slides of forensic casework as well as serving as a probe for seminal fluid using ELISA or radioimmunoassay.

It is of evolutionary interest to find the MHS-5 antigen in several Pongids (chimpanzee, gorilla, and orangutan) that are close human relatives and not in members of more distantly related primate species. Although the ideal forensic semen probe should be one that cross-reacts with no other animal's semen, the likelihood of Pongid primates being considered rape suspects is slight, and the cross-reactivity with semen of closely related primates should not detract from the application of the monoclonal in forensic analysis.

The MHS-5 hybridoma has demonstrated continued immunoglobulin secretion in culture for 14 months and has been frozen and recovered repeatedly. Three separate groups of mice have produced monoclonal antibody ascites with this line, averaging 27 mg IgG/ml. Using the criterion for positivity of an OD greater than twice the background OD, each of these ascites demonstrated titers greater than 1:50,000 on wells coated with 10 $\mu$g seminal fluid protein. Thus, the MHS-5 clone has demonstrated its stability and shown adequate levels of immunoglobulin secretion as an ascites tumor. Good yields from a scaled up production of this monoclonal antibody can be expected.

Monoclonal immunoreagents offer advantages of uniformity, specificity, constant affinity, and availability in virtually unlimited supply over their polyclonal counterparts. The MHS-5 monoclonal probe provides the opportunity for forensic laboratories to standardize semen identification and compare results from one laboratory with another, and may given an added measure of certainty to testimony by the forensic specialist. The forensic semen markers currently in use, P30 and acid phosphatase, are secretory products of the prostate gland. The MHS-5 antigen is the first marker protein from the human seminal vesicles proposed for sexual assault analyses employing a monoclonal antibody probe.

Homogentates were made of various reproductive tract organs obtained at autopsy. Tissues were obtained within several hours of death to minimize necrosis and antigen autolysis or displacement. Specimens were obtained from patients who had died of a variety of diseases, the ages of the patients ranging from 60 to 89 years. Seminal vesicle, prostate, testis epididymis, kidney, liver, spleen, and pancreas were obtained from 10 cadavers and homogenized in carbonate-bicarbonate buffer, pH 9.2 with a Precision Scientific tissue homogenizer. Homogenates were centrifuged for 10 minutes at $500\times g$ and the remaining supernatants were precipitated with 90% cold acetone. A pellet of the precipitated proteins, obtained after centrifugation at $500\times g$, was resuspended in the coating buffer for subsequent ELISA assay as above.

Pooled seminal fluid from vasectomized donors was lyophilized overnight with a FTS Dura-Dry lyophilizer. To determine the amount of seminal fluid antigen necessary to completely absorb the MHS-5 antibody, varying amounts of seminal fluid lyophilysate ranging from 27 mg to $2.7\times 10^{-4}$ ng were added to 1-ml aliquots of murine ascites (1/100,000) containing the MHS-5 antibody (270 ng IgG per 1 ml) so that solutions containing antibody and seminal fluid powder in ratios ranging from 1:105 to $1:10^{-5}$ were obtained. After immunoprecipitation overnight at 7° C., pellets were obtained by centrifugation at $500\times g$ for 10 minutes, and the supernatants were tested for residual antibody activity against seminal fluid (100 $\mu$g coated per well) by ELISA. The data obtained by this method were used to develop a completely absorbed antibody control for immunocytochemistry.

Human seminal vesicles obtained during radical retropubic prostatectomy were fixed in 10% formalin in PBS, pH 7.2, and embedded in paraffin. Specimens from three subjects were examined. Sections 6 $\mu$m thick were deparaffinized in xylene and hydrated through a graded alcohol series and rinsed in distilled water. Sections were incubated in 0.3% $H_2O_2$ in absolute methanol for 30 minutes to block endogenous peroxidase, then washed for 20 minutes in PBS, pH 7.6, and blocked for 30 minutes in 3% normal goat serum diluted in PBS, pH 7.6. The following tissues were fixed and processed in an identical manner: normal prostate, testis, epididymis, bladder, kidney, colon, and breast; adenocarcinoma of prostate, kidney, colon, and breast; and transitional cell carcinoma of bladder, testicular seminoma, and teratocarcinoma.

A 1/100 dilution of the MHS-5 monoclonal antibody ascites (27 $\mu$g IgG per 1 ml) in PBS, pH 7.6, was used as a primary antibody with the sections incubated for 30 minutes. After a 10minute wash in 250 ml of PBS, the sections were incubated for 30 minutes in a 1:200 solution of biotin-labeled goat antimouse IgG secondary antibody (Vector, Burlingame, CA) and washed again in PBS. The sections were incubated in 10 $\mu$g/ml avidin with 2.5 $\mu$g/ml biotin peroxidase (Vector) in PBS for 45 minutes, followed by another 10-minute wash in 250 ml PBS. Hydrogen peroxide (0.01%) and 0.05% diaminobenzidine hydrochloride (DAB; Sigma, St. Louis) in PBS, pH 7.2, were used to develop a brown reaction product. The sections were rinsed for 5 minutes in running water, mounted, and examined under a Leitz Ortholux microscope equipped with Leitz NPL Fluotar 16X, 40X, and 100X objectives. Bright-field photographs were taken on a Leitz Orthomat camera using Kodachrome 40 ASA 35-mm film. Control sections were treated in an identical fashion except for lack of primary antibody or lack of secondary antibody to assess for nonspecific antibody binding; DAB without antibodies to assess endogenous peroxidase; and an absorbed control consisting of 270 ng MHS-5 IgG absorbed with 2.7 mg seminal fluid powder (determined by absorption experiments above).

Epididymal sperm were obtained at vasovasotomy from one patient and assessed for the MHS-5 antigen by ELISA. Epididymal sperm were incubated for 2 hours at 37° C. with 1) secretions from the seminal vesicle lumen obtained from cadavers, or 2) with seminal fluid from vasectomized donors. In addition, cells from a human lymphoblastoid line, LICR-LOR HMY2 (Edwards et.al., A Human-Human Hybridoma System Based on a Fast-Growing Mutant of the ARH-77 Plasma Cell Leukemia Derived Line, EUR J IMMUNOL, 12:641-648 (U.S.A. 1982)) were treated in an identical fashion. Both were assessed for reactivity with the MHS-5 antibody by ELISA following incubation. Positive controls consisted of seminal fluid from vasectomized males (10 μg coated per well) and seminal vesicle secretion from cadavers (100 μg per well). BSA was used as a negative control (100 μg per well).

Figure 9:
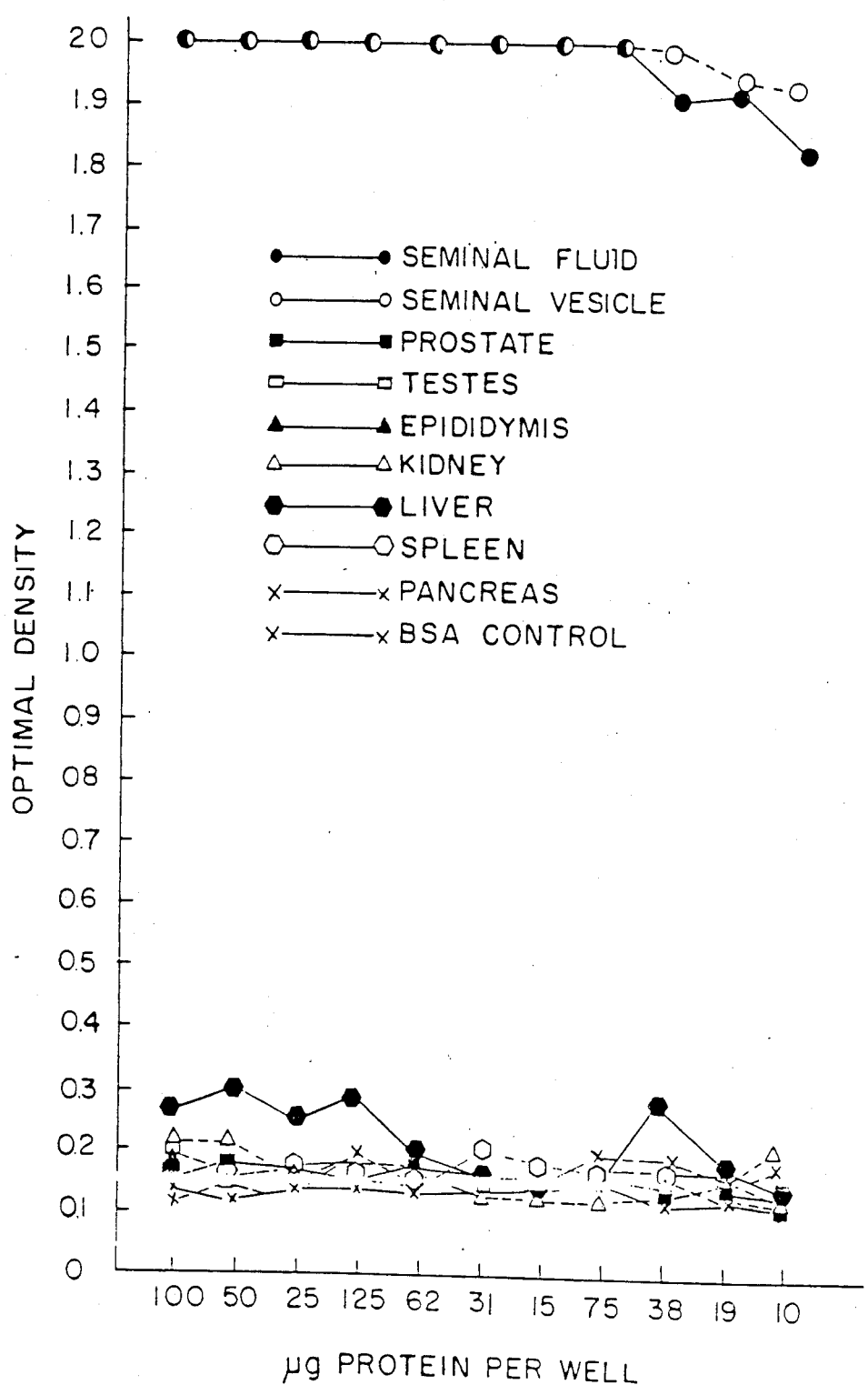
FIG. 9 is a graph depicting results from ELISA testing seminal fluid from normal donors in tissue homogenates from seminal vesicle, prostate, testes, epididymis, kidney, liver, spleen, pancreas and BSA control. The MHS-5 antigen was found to localize in the seminal vesicles.

In FIG. 9 the results of an ELISA assay for the MHS-5 antigen in homogenates of reproductive organs from 10 autopsies is presented. Seminal vesicle homogenates and seminal fluid gave optical density readings (OD) of 2, the maximum reading on the Multiscan plate reader, whereas homogenates of other reproductive tract organs gave OD readings similar to the BSA-negative control (OD approximately 0.15). These results indicate that the MHS-5 antigen is located in the seminal vesicle. To further check possible cross-reactivity of the MHS-5 antibody, homogenates of kidney, pancreas, spleen, and liver were tested by ELISA and gave background OD readings, confirming specificity of the MHS-5 monoclonal antibody for an antigen originating in the human seminal vesicle.

Figure 10:
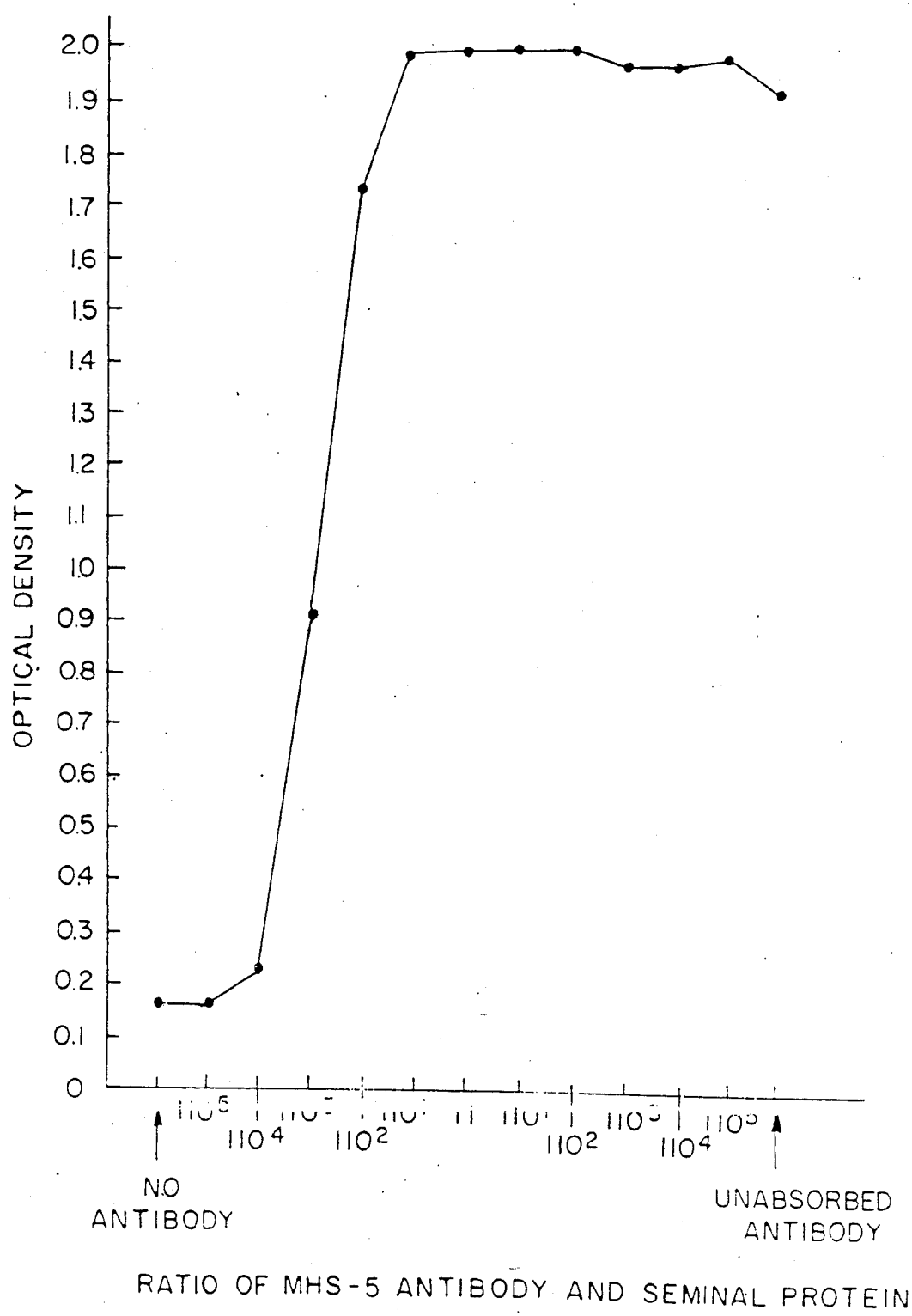
FIG. 10 is a graph depicting results from ELISA testing for the titration of a constant amount of MHS-5 monoclonal antibody with seminal fluid lyophilysate, measuring residual antibody activity.

FIG. 10 shows the results of ELISA assay of supernatants remaining after immunoprecipitation of a constant amount of MHS-5 antibody with varying amounts of lyophilized seminal fluid. Antibody activity of the MHS-5 monoclonal antibody ascites began to decline following incubation with lyophilized seminal fluid at a ratio of 1/10 and was completely absent following incubation of monoclonal antibody with a 10,000-fold excess of seminal fluid lyophilysate. On the basis of this curve, in order to obtain a negative control for immunohistochemical localization experiments, 270 ng MHS-5 IgG was completely absorbed with 2.7 mg seminal fluid lyophilysate.

Figure 11:
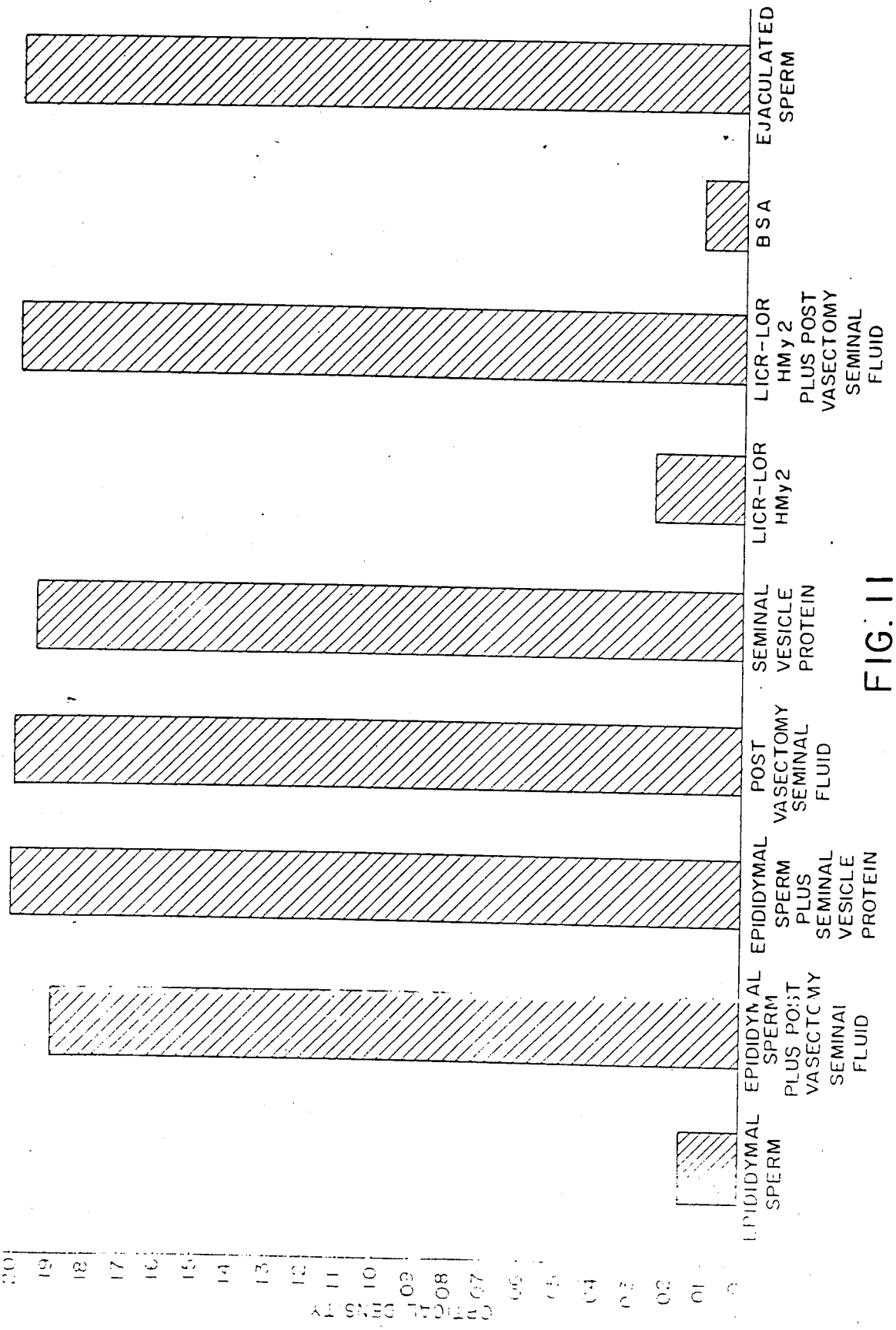
FIG. 11 is a bar graph depicting results from ELISA testing for the presence of the MHS-5 antigen on epididymis sperm, epididymis sperm incubated with vasectomized semen, or protein obtained from the seminal vesicle lumen. Antibody binding to semen from a vasectomized donor, to proteins from the seminal vesicle, and to ejaculated sperm are shown (positive controls). BSA-coded wells served as negative controls. Reconstitution of the MHS-5 antigen on the surface of the normally antigen-negative lymphoblastoid line, LICR, is also presented.

To specifically study the MHS-5 antigen's association with epididymal sperm, samples were obtained at vasovasostomy and tested for reactivity with the monoclonal antibody on ELISA. As can be seen in FIG. 11, the optical density reading for epididymal sperm was similar to negative control values (BSA), whereas ejaculated sperm reacted strongly with the antibody. These data suggested that the MHS-5 antigen adhered to the sperm surface during ejaculation. To test this hypothesis, epididymal sperm were incubated with seminal fluid from vasectomized males or with secretions obtained at autopsy from the seminal vesicle lumen. These sperm samples were then washed and tested by ELISA for the presence of the MHS-5 antigen. Sperm treated in this fashion gave OD readings equal to those obtained for ejaculated sperm, demonstrating that the antigen can be reconstituted on the sperm surface. Treatment of the human lymphoblastoid line LICR in an identical manner caused the normally antigen negative lymphoblastoid cells to test positive for the MHS-5 antigen. This result indicated that the MHS-5 antigen does not have specificity for sperm, but will coat the surface of another cell type.

A hematoxylin and eosin stain of sectioned human seminal vesicle tissue is presented in the photomicrograph in FIG. 12A. The seminal vesicle is a coiled tubular gland. Circular profiles of pseudostratified, tall columnar epithelium are seen surrounded by a fibrous connective tissue stroma with slips of smooth muscle occasionally present in connective tissue septae. Indirect immunolocalization employing the MHS-5 monoclonal antibody, biotinylated goat antimouse IgG, and peroxidase-avidin, demonstrated dark brown immunoreactive product in the epithelium of the human seminal vesicle (FIGS. 12C, D). No appreciable reaction product was evident in the connective tissue compartment. The seminal antigen-absorbed control (FIG. 12B), as well as the controls of primary antibody without second antibody and secondary antibody without primary antibody, showed no immunolocalization. An occasional dark reaction spot was visible in seminal vesicle material incubated with DAB alone. This brown reaction was due to lipofuchsin granules which are know to accumulate in aged seminal vesicles.

Virtually every columnar epithelial cell lining the lumen of the seminal vesicle ductwork demonstrated an immunoreactive when incubated with the MHS-5 monoclonal antibody. At high magnifications (4d) the reaction product was absent within the nucleoplasm of several nuclei, although other nuclear profiles appear to contain reaction product. It was difficult by light microscopy to ascribe this apparent reaction to nucleoplasm itself or to cytoplasm that might have overlain the nuclei in the section.

Paraffin sections of normal prostate, testis, epididymis, bladder, kidney, colon and breast; adenocarcinoma of prostate, kidney, colon and breast; and transitional cell carcinoma of bladder, testicular seminoma and teratocarcinoma were examined by immunocytochemistry and showed no binding of the MHS-5 monoclonal antibody. In each experiment on these other tissue types, human seminal vesicle was included as a positive control and in each case positive localization to seminal vesicle epithelium was observed.

The specificity of the MHS-5 monoclonal antibody for an antigen of human seminal vesicle origin is supported by complementary data from immunoassay and immunohistochemistry. ELISA testing of tissue homogenates from 10 cadavers demonstrated the MHS-5 antigen only in seminal vesicle homogenates and in no other male reproductive tissues or splanchnic organs. The advanced age of certain patients did not diminish the detectability of the MHS-5 antigen in the seminal vesicle, as there was no difference in the reactivity of the MHS-5 antibody to homogenates obtained from the oldest patients (aged 80-90; N=3) compared to homogenates from younger patients (aged 60-70, N=4).

The localization of the MHS-5 antigen within the human seminal vesicle is confirmed by immunohistochemical studies. The antigen was found within the cytoplasm of the epithelial cells that line the lumen of the seminal vesicle. The surrounding stromal tissue did not react with the MHS-5 monoclonal antibody; nor could the antigen be detected in sections of normal prostate, testis, epididymis, bladder, kidney, colon, or breast. Further, the MHS-5 monoclonal antibody did not bind to sections of adenocarcinoma of the prostate, kidney, colon, or breast, to transitional cell carcinoma of the bladder or to testicular seminoma, teratocarcinoma, or embryonal cell carcinoma, although sections of seminal vesicle run in parallel with these tumor tissues gave good immunolocalization.

Originally identified in semen, the MHS-5 antigen's localization to the seminal vesicle epithelium suggests that the antigen is synthesized and secreted by this tissue. Also there is no cross-reactivity with blood, suggesting that the antigen is not a serum component that transudates from the circulation to be concentrated by the seminal vesicle epithelium.

The human seminal vesicle epithelium contains two cell populations, basal cells and principal cells. Principal cells have been shown to contain abundant rough endoplasmic reticulum, numerous secretory granules, and a well-developed Golgi apparatus. Basal cells have a less well-developed Golgi apparatus and rough endoplasmic reticulum and do not appear cytologically to be a major secretory cell type. Principal cells constitute the majority of the cells within the seminal vesicle epithelium. Because the immunolocalization of the MHS-5 antigen appears in virtually every cell that lines the lumen of the human seminal vesicle, it is clear that the principal cells contain the MHS-5 antigen. Whether basal cells also contain the MHS-5 antigen could not be determined and must be examined by further ultrastructural study.

Inasmuch as the MHS-5 monoclonal antibody did not react with human epididymal sperm but did bind to ejaculated sperm on ELISA, and could be reconstituted on epididymal sperm by incubation with semen from vasectomized males, the MHS-5 antigen may be considered to be a "sperm-coating antigen" that originated within the human seminal vesicle and coated the human sperm surface during ejaculation. Weil and Rodenbury defined a sperm-coating antigen as "a substance secreted by the male accessory glands that binds tightly to the sperm surface and cannot be removed by washing". Antisera produced against sperm-coating antigens will react with ejaculated but not epididymal sperm, Weil et.al., *Immunological Differentiation of Human Testicular (Spermatocele) and Seminal Spermatozoa*, PROC SOC EXP BIOL MED, 105:43–45 (U.S.A. 1960).

At least six sperm-coated antigens have been identified in human seminal plasma. The antigen lactoferrin and seminal plasma No. 7 antigen (ferrisplan) are two sperm-coating antigens that have been shown to be of vesicular origin. Using immunofluorescence and a monoclonal antibody to ferrisplan, Koyama and co-workers showed that the epithelial cells of the human seminal vesicle secreted the ferrisplan antigen, which was then found on the postnuclear cap and midpiece segment of ejaculated spermatozoa, Koyama et.al., *Localization of Human Seminal Plasma No. 7 Antigen (Ferrisplan) in Accessory Glands of the Male Genital Tract*, J REPROD IMMUNOL, 5:135-143 (U.S.A. /1983).

Wahlstrom and co-workers discovered placental protein 5 (PP5) in the seminal plasma and used a polyclonal rabbit anti-PP5 antiserum and an immunoperoxidase staining technique to localize PP5 to the seminal vesicle epithelium, Wahlstrom et.al., *Immunohistochemical Demonstration of Placental Protein t (PP5)-like Material in the Seminal Vesicle and the Amoullar Part of the Vas Deferens*, LIFE SCI, 31:2723–2725, (U.S.A. 1982). PP5 does not function as a sperm-coating antigen. Wahlstrom and Ranta also demonstrated that prolactin (also a noncoating antigen) is present in human seminal vesicle secretion, Wahlstrom et.al., *Accumulation of Prolactin in Human Seminal Vesicles As Revealed By Immunohistochemical Studies*. FERTIL STERIL, 40:545-48 (U.S.A. 1983); however, it localizes to a perivascular cell population located in the venous plexuses between the folds of the seminal vesicle walls and not to seminal vesicle epithelial cells.

The MHS-5 antigen is distinct from previously described seminal vesicle antigens as determined by a comparison of the molecular weights of other seminal protein antigens with MHS-5. The molecular weight of the MHS-5 antigen has been determined by immunoblot analysis of reduced peptides in liquefied ejaculates from vasectomized men. In semen liquefied for 15 hours three peptides of 10, 11.9 and 13.7 kD were the most immunoreactive species. The molecular weight of ferrisplan under reduced conditions is 15 kD; that of prolactin is 22 kD; that of lactoferrin is 80 kD; and PP5 is 36 kD. Thus on the basis of molecular weight considerations the MHS-5 antigen appears to be a protein secreted by the seminal vesicle epithelium that has not been previously described.

Because the MHS-5 monoclonal antibody (1) did not bind to any other human biological fluid tested by ELISA, (2) did not bind to nonseminal vesicle tissue sections tested, and, to seminal vesicle epithelium, it may prove clinically useful as a marker for the human seminal vesicle epithelium. Such a specific probe for human seminal vesicle epithelium has potential clinical application in the diagnostic procedures employed to detect prostatic adenocarcinoma. In the treatment of adenocarcinoma of the prostate a definitive diagnosis of adenocarcinoma must be made prior to surgical or radiologic treatment. Fine-needle aspiration biopsy has been used in Scandinavia for many years and is becoming more popular in this country. One potential source of false-positive results is contamination of the sample with seminal vesicle cells following transrectal aspiration biopsy. These cells may be misdiagnosed as carcinoma especially in older men, because they often contain large hypochromatic nuclei that are similar in appearance to prostatic carcinoma. Because the MHS-5 monoclonal antibody recognizes seminal vesicle epithelium specifically, staining of biopsy or cytology specimens with the MHS-5 monoclonal antibody by the biotin-avidin-peroxidase or other techniques may help to eliminate misidentifications of seminal vesicle epithelial cells. Neither adenocarcinoma of the prostate nor normal prostate reacts with MHS-5 antibody on histological material, further supporting a possible clinical application of the MHS-5 monoclonal antibody probe as a marker for seminal vesicle epithelial cells in aspiration biopsy cytology.

Figure 13:
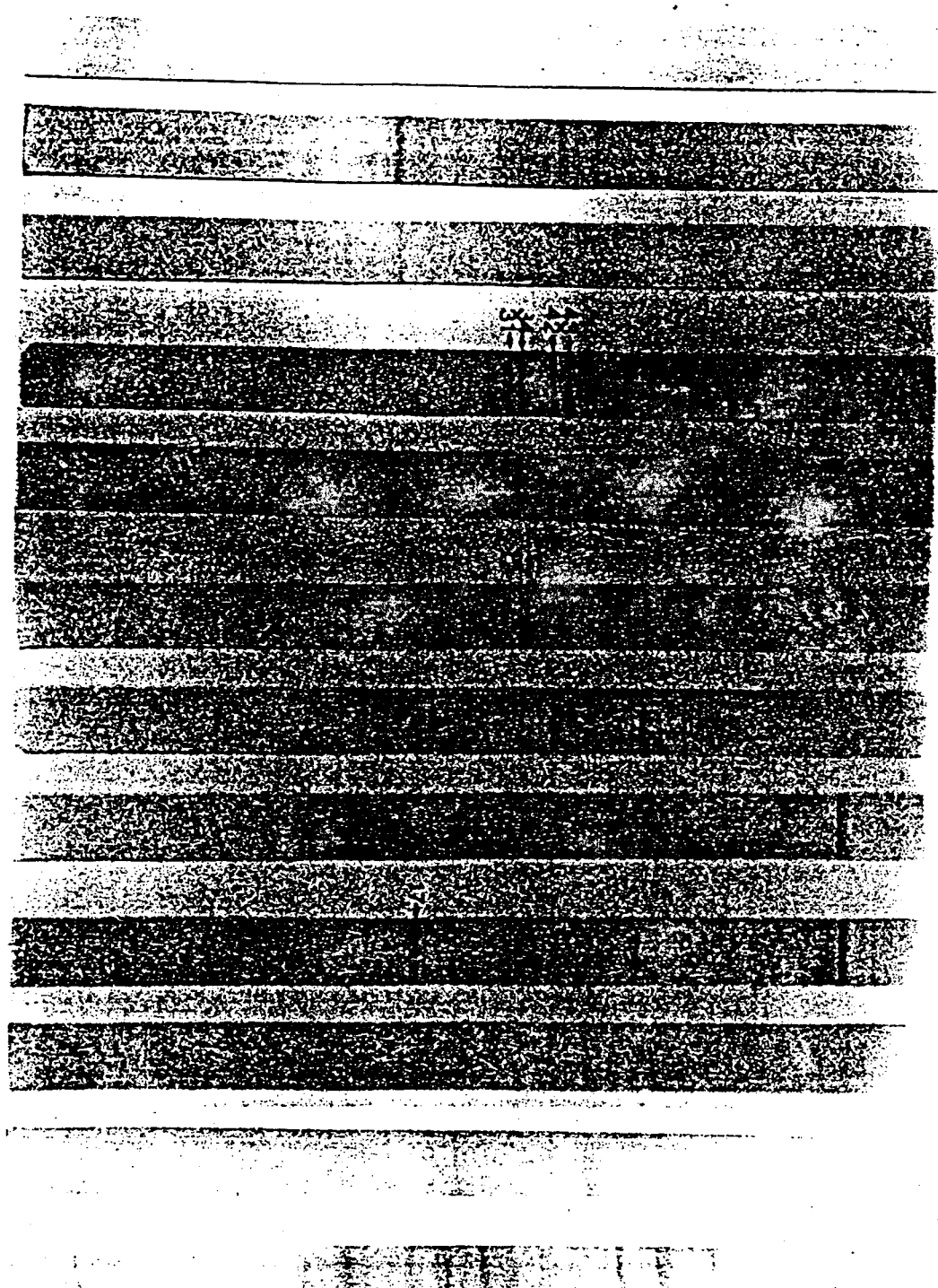
FIG. 13 shows a Western blot of a panel of monoclonal antibodies raised to human serum and seminal fluid.

Additional fusions have been performed. Of 32 hybridomas which we have produced to human sperm and seminal fluid, one additional antibody (termed MHS-4) has shown immunoreactivity with the identical peptides that are recognized by MHS-5 in a fresh human ejaculate. The accompanying FIG. 13 shows a Western blot of a panel of monoclonal antibodies raised to human sperm and seminal fluid. The dark bands on the nitrocellulose blot represent the binding of different purified monoclonal antibodies to proteins extracted from human sperm. These monoclonals were arranged according to their immunoblot staining patterns. It can be seen that monoclonal antibody MHS-1 and MHS-2, for example, each recognize four bands arranged as doublets of 43-42 and 34-31 kilodalons. Monoclonal antibodies MHS-4 and MHS-5 show identical binding to each other on these extracts of ejaculated sperm membranes. This provides evidence that other monoclonal antibodies to the same seminal vesicle specific antigen recognized by the MHS-5 monoclonal have been developed.

While the invention has been described with reference to specific embodiments, modifications and variations of the invention may be constructed without departing from the scope of the invention, which is described in the following claims.

We claim:

1. A monoclonal antibody which specifically binds to a seminal vesicle specific antigen, SVSA, wherein SVSA is secreted by principal cells of the seminal vesicle epithelium, and wherein further the antibody is MHS-5.

2. A method for producing an antibody which specifically binds to a seminal vesicle specific antigen secreted by principal cells of the seminal vesicle epithelium, comprising the steps of:

(a) collecting a human antigen from seminal vesicles distal from epididymides, said antigen not being present in the epididymides;

(b) immunizing a creature having an immune system with said antigen;

(c) obtaining B lymphocytes from said immunized creature; and (d) fusing said lymphocytes with myeloma cells, whereby a hybridoma is produced that produces monoclonal antibodies to said antigen;

wherein the antibodies are MHS-5.

* * * * *